United States Patent
Ichihara

(10) Patent No.: US 9,131,877 B2
(45) Date of Patent: Sep. 15, 2015

(54) LASER APPARATUS AND PHOTOACOUSTIC APPARATUS

(71) Applicant: CANON KABUSHIKI KAISHA, Tokyo (JP)

(72) Inventor: Shigeru Ichihara, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/034,966

(22) Filed: Sep. 24, 2013

(65) Prior Publication Data

US 2014/0092932 A1    Apr. 3, 2014

(30) Foreign Application Priority Data

Oct. 2, 2012    (JP) .................. 2012-220134

(51) Int. Cl.

| | | |
|---|---|---|
| H01S 3/10 | (2006.01) | |
| A61B 5/145 | (2006.01) | |
| H01S 3/102 | (2006.01) | |
| G01H 9/00 | (2006.01) | |
| H01S 3/106 | (2006.01) | |
| H01S 3/08 | (2006.01) | |
| H01S 3/092 | (2006.01) | |
| H01S 3/115 | (2006.01) | |
| H01S 3/136 | (2006.01) | |

(52) U.S. Cl.
CPC .. *A61B 5/14* (2013.01); *G01H 9/00* (2013.01); *H01S 3/106* (2013.01); *H01S 3/1026* (2013.01); *H01S 3/08004* (2013.01); *H01S 3/08054* (2013.01); *H01S 3/08059* (2013.01); *H01S 3/08072* (2013.01); *H01S 3/092* (2013.01); *H01S 3/115* (2013.01); *H01S 3/136* (2013.01)

(58) Field of Classification Search
CPC ..... H01S 3/0823; H01S 3/1026; H01S 3/082; H01S 3/106; H01S 3/08004; G01H 9/00; A61B 5/14
USPC ....................... 372/100, 20; 73/655
See application file for complete search history.

(56) References Cited

U.S. PATENT DOCUMENTS

| | | | | |
|---|---|---|---|---|
| 6,078,606 | A | * | 6/2000 | Naiman et al. ............. 372/97 |
| 2012/0318066 | A1 | | 12/2012 | Ichihara et al. ............ 73/655 |
| 2013/0070802 | A1 | | 3/2013 | Ichihara .................. 372/70 |
| 2014/0031667 | A1 | | 1/2014 | Ichihara et al. ............ 600/407 |

FOREIGN PATENT DOCUMENTS

| | | | | |
|---|---|---|---|---|
| JP | 2007-248304 | * | 3/2006 | ............ G01S 7/48 |
| JP | 2007-248304 | | 9/2007 | |

OTHER PUBLICATIONS

S. Manohar et al., "Region-of-Interest Breast Studies Using the Twente Photoacoustic Mammoscope (PAM)", *Proc. Of SPIE*, vol. 6437 643702-1 (2007).

* cited by examiner

*Primary Examiner* — Tuan Nguyen
(74) *Attorney, Agent, or Firm* — Fitzpatrick, Cella, Harper & Scinto

(57) ABSTRACT

A laser apparatus that allows selection of a wavelength of output light from a plurality of options. The laser apparatus includes: a resonator made up from an output mirror and reflection means having a plurality of reflective surfaces fixed in position; a laser medium disposed on an optical axis inside the resonator; branch means branching an optical path of a light beam formed on the optical axis when light oscillates in the laser medium into a plurality of optical paths having an end at one reflective surface of the reflection means, the branch means forming a first optical path coinciding with the optical axis when located out of the optical axis, and forming a branch path by moving the light of the optical axis parallel when located on the optical axis.

31 Claims, 13 Drawing Sheets

LASER APPARATUS AND PHOTOACOUSTIC APPARATUS

BACKGROUND OF THE INVENTION

1. Field of the Invention

The present invention relates to a tunable laser apparatus and a photoacoustic apparatus that uses this laser apparatus.

2. Description of the Related Art

Photoacoustic tomography (PAT) apparatuses that use lasers for medical applications have been developed (see Non-Patent Literature 1). PAT apparatuses are expected to be used for determination of presence or absence of a tumor through observation of blood vessels congregating around a tumor in a living body, or for functional analysis of tissues based on the differences between oxyhemoglobin and deoxyhemoglobin spectra.

A PAT apparatus emits nanosecond laser pulses to a segment being measured and analyses received signals converted from ultrasound waves (photoacoustic waves) generated by the photoacoustic effect to obtain an image. As the light intensity decays by diffusion in the living body, it is necessary to emit laser beams with high energy per pulse to obtain a photoacoustic wave from a segment relatively deep in a living body such as a breast, in particular.

Some lasers called tunable lasers that use titanium sapphire or alexandrite, which is a laser medium with a broad gain bandwidth, allow selection of a wavelength. Generally, to induce laser oscillation at a desired wavelength, tunable lasers use a wavelength selection mechanism that includes an optical element such as a prism, a diffraction grating, or a birefringent plate. The optical element is arranged on an optical axis inside a resonator and mechanically moved to allow selection of a wavelength at which oscillation should take place.

If a prism is used as an element of the wavelength selection mechanism, generated beams of respective wavelengths are resonated in the resonator correspondingly to the angular deviation of the optical paths that is determined by the refractive index of the prism. If the prism itself is used as a reflective mirror of the resonator, the prism is mechanically rotated in the plane of the substrate forming the resonator. If a separate reflective mirror is used with the prism, the prism is fixed in position, while the reflective mirror located correspondingly to the angular deviation of the optical path of respective wavelengths is mechanically rotated.

If a diffraction grating is used as an element of the wavelength selection mechanism, a reflective mirror is mechanically rotated in accordance with an oscillating wavelength for selection of the target wavelength, as with the prism.

If a birefringent plate is used as an element of the wavelength selection mechanism, the birefringent plate is mechanically rotated such as to maintain the angle of the optical axis of the beam being resonated relative to the incident and exit surfaces of the birefringent plate at a constant angle.

In another known method (Patent Literature 1), light of two different wavelengths is produced at the same time in the resonator, and with a wavelength selective filter disposed outside the resonator inserted onto the optical axis or retracted from the optical axis, a target wavelength is selected.
Patent Literature 1: Japanese Patent Application Laid-open No. 2007-248304
Non-Patent Literature 1: S. Manohar et al, Proc. of SPIE vol. 6437 643702-1

SUMMARY OF THE INVENTION

To detect a spectral difference between oxyhemoglobin and deoxyhemoglobin with a PAT apparatus, it is necessary to irradiate the object with laser beams of at least two wavelengths and to compare the intensities of signals representative of the photoacoustic waves obtained at respective wavelengths. Since the signal intensity is affected by the conditions of the living body and measurement conditions such as measurement positions, it is preferable that the measurement conditions other than the wavelength be the same when comparing the signals obtained at respective wavelengths. It is therefore desirable that the time required for changing the wavelength be as short as possible to obtain measurements before the living body condition undergoes any changes.

It is also necessary to minimize optical path angular deviation and wavelength shift when changing the wavelength. Other requirements include stable laser output, and wavelength stability (no fluctuations) at each wavelength.

Considering that a PAT apparatus is used in a hospital or medical examination facility, it is preferable that the laser used for this purpose has high stability and requires no adjustment for correcting optical path angular deviation and wavelength shift.

Conventional tunable lasers, if applied to a PAT apparatus, would have the following problems, in consideration of the requirements described above.

Conventional mechanisms for changing the wavelength that use a prism or a diffraction grating control the position of a reflective mirror by rotating it with a stage or the like. Any displacement of rotational position of the reflective mirror would lead to wavelength fluctuation. Any displacement of the shifting or tilting angle of the reflective mirror would lower the laser output resulting from the misalignment. It is therefore necessary to move the stage position precisely each time the wavelength is changed (e.g., for each emitted pulse), and to make the stage stable and still during laser oscillation. That is, the stage has to be rotated and stopped each time the wavelength is changed.

Even a driving stage made from highly reliable components would have limited durability if subjected to such repeated operations.

To achieve laser output stability, it is essential to keep thermal stability of the resonator in the application environment of the laser. Generally, aluminum is used for the laser substrate. Use of a high durability component made of a material other than aluminum could possibly cause a problem in keeping the thermal stability of the entire resonator due to different thermal expansion coefficients of the components.

A wavelength changing mechanism that uses a birefringent plate is large in size as it requires a combination of plural birefringent plates. The problem in such a mechanism would be the controlling of rotation of the large birefringent plates that have to be rotated and stopped every time the wavelength is changed. This problem would be more evident when changing the wavelength for each laser pulse, and even more so as the laser pulse frequency is increased. Should a difficulty arise in the control and the rotation precision is degraded, the selected wavelength would be shifted from the target one.

In view of the problems described above, it is preferable to use a wavelength changing mechanism with little possibilities of wavelength shift and optical path angular deviation.

There is the method, as shown in Patent Literature 1, of selecting one of two wavelength laser beams by inserting a wavelength selective filter onto the optical axis or retracted therefrom outside the resonator. This method of selecting a wavelength outside the resonator is free of the problem of optical path deviation. However, the method is disadvantageous in terms of cost, as it requires a special configuration for producing light of two wavelengths inside the resonator.

Moreover, since one of the two output laser beams is shut off by the filter, the energy use efficiency is low, so that it is not suited to applications where high output energy is required.

The present invention was made in view of the problems described above. An object of the invention is to provide a laser apparatus having a wavelength selection mechanism with a simple structure and with little possibilities of wavelength shift and optical path angular deviation.

The present invention provides a laser apparatus that allows selection of a wavelength of output light from a plurality of options, comprising:

a resonator made up from an output mirror and a reflection means having a plurality of reflective surfaces fixed in position;

a laser medium disposed on an optical axis inside the resonator;

a branch means branching an optical path of a light beam formed on the optical axis when light oscillates from the laser medium into a plurality of optical paths having an end at one reflective surface of the reflection means, the branch means forming a first optical path coinciding with the optical axis when located out of the optical axis, and forming a branch path by moving the light of the optical axis parallel when located on the optical axis; and a moving means moving the branch means between a position on the optical axis and a position out of the optical axis, wherein the reflective surface determining a wavelength of output light.

The present invention can thereby provide a laser apparatus having a wavelength selection mechanism with a simple structure and with little possibilities of wavelength shift and optical path angular deviation.

Further features of the present invention will become apparent from the following description of exemplary embodiments with reference to the attached drawings.

DESCRIPTION OF THE EMBODIMENTS

Preferred embodiments of the present invention will be hereinafter described with reference to the drawings. Note, it is not intended to limit the scope of this invention to the specifics given below, and the sizes, materials, shapes, and relative arrangements or the like of constituent components described below should be changed as required in accordance with the configurations and various conditions of the apparatus to which the invention is applied.

The present invention can be understood as a tunable laser apparatus, and a control method of the same. The present invention can be applied to a photoacoustic apparatus including such a tunable laser apparatus as one constituent element. Namely, a photoacoustic apparatus having a tunable laser apparatus according to the present invention to irradiate an object with laser light to obtain a photoacoustic wave that is generated from a light absorbing part inside the object by the photoacoustic effect and propagates through the object. With the use of the tunable laser apparatus according to the present invention, the wavelength of light emitted to the object can be changed simply in a stable manner, so that presence of various tissues (light absorbing parts) having different light absorption characteristics can be identified as property information.

The acoustic waves referred to in the present invention are typically ultrasound waves, including elastic waves that are called sound waves, ultrasound waves, or acoustic waves. An acoustic wave generated by the photoacoustic effect is referred to as a "photoacoustic wave", or a "light-induced ultrasound wave".

Embodiment 1

The configurations of various wavelength changing mechanisms in the laser apparatus will be described below in respective embodiments.

(Basic Configuration with Parallel Plate)

Figure 1:
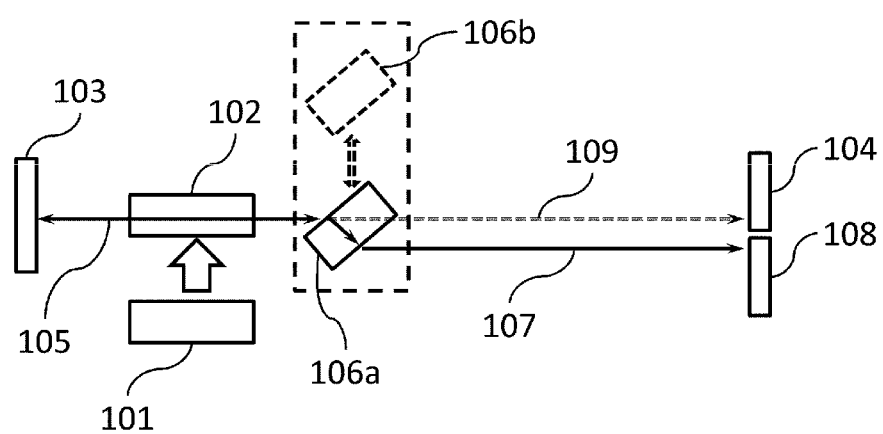
FIG. 1 is a configuration diagram illustrating one embodiment of a laser apparatus of the present invention.

FIG. 1 is a configuration diagram of a laser resonator in this embodiment.

A pumping light source 101 is a light source for exciting a laser medium 102. An output mirror 103 and a reflective mirror 104 form the laser resonator having an optical axis 105 of light reflected between them. A parallel plate 106 is a branching optical element in this embodiment, and moves between position 106a on the optical axis 105 and position 106b offset from the optical axis 105. A branch path 107 is the optical path formed when the parallel plate 106 is inserted onto the optical axis. A reflective mirror 108 is arranged on the branch path 107, thereby forming the resonator with the output mirror 103. The optical path formed when the parallel plate 106 is moved out of the optical axis will be referred to as first optical path 109. Here, the first optical path 109 and the optical axis 105 lie on the same line.

On the output mirror 103 is deposited a dielectric film that defines the transmissivity of a given wavelength for laser oscillation at a desired wavelength. The laser medium 102 is a gain medium having a broad oscillation band such as, for example, titanium sapphire (Ti:sa) or alexandrite. The reflection unit includes the reflective mirror 104 and a different reflective mirror 108, which are each disposed to reflect light of a desired wavelength in the oscillation band of the laser medium 102, and include a reflective film of dielectric material suitable for the respective wavelengths. Here, the plurality of (two) reflective mirrors each form a reflective surface.

In the present invention, the central wavelength is adjusted to be a desired wavelength, which has different spectral line widths depending on what type of reflection means is used. A small line width need not necessarily be the top priority, considering that efficient high energy output is required. For use in a laser apparatus of a photoacoustic system in diagnostic applications, in particular, a laser beam with a relatively broad spectral line width can be used without any problems.

For the pumping light source 101, a laser light source excited by a lamp or semiconductor laser, or a lamp may be used in accordance with the applications. If the laser medium is Ti:sa, it is commonly pumped by a laser beam of around 500 nm. Preferably, it should be pumped by a laser beam having a second harmonic of Nd:YAG laser, which is 532 nm. If the laser medium is alexandrite, it should preferably be pumped by a lamp. To produce laser pulses for use in a photoacoustic apparatus, a flash lamp may be used for the pumping and a Q-switch (Q-sw) (not shown) including a Pockels cell or the like may be disposed on the optical axis between the output mirror 103 and the laser medium 102.

A comparison between the first optical path 109 (coaxial with the optical axis 105) formed when the parallel plate 106 retracts from the optical axis 105 and is located at position 106b, and the branch path 107 formed when the parallel plate 106 is inserted onto the optical axis 105 and located at position 106a shows that they are parallel and correspond to the reflective mirrors 104 and 108, respectively. The optical paths are thus changed by moving the parallel plate 106 onto the optical axis 105 and out of the optical axis 105, so that the oscillating wavelengths can be switched.

The parallel plate 106 should preferably be made of a material having a high refractive index and high laser resistance, such as quartz. In order to reduce the losses when light transmits through the parallel plate 106, the parallel plate 106 should preferably be arranged at a Brewster angle relative to the incident light. For minimizing the losses, dielectric anti-reflection films may be provided to incident and exit surfaces.

Whether the optical paths can be switched or not by the parallel plate does not depend on the position of the parallel plate 106 on the optical axis 105 or the distance by which the parallel plate 106 is moved onto the optical axis 105. Namely, even if the parallel plate is slightly displaced from the position where it is supposed to be, angular deviation of the optical path is unlikely to occur, so that there is little possibility of errors such as stop or reduction of lasing power caused by a misalignment in the resonator.

If the parallel plate is slightly displaced, the position of the light beam incident on the reflective mirror will be slightly changed. However, this does not affect laser output or the like, since the position of the light beam passing through the laser medium remains the same. In other words, a displacement of the parallel plate does not cause an angular deviation of the optical path, so that the branch path remains parallel to the first optical path. If the reflective mirror is provided with a reflective film of dielectric material having uniform characteristics, there will hardly be any wavelength shift, either, since there are no wavelength fluctuations.

It can be seen from the above that the use of a parallel plate as the branching optical element enables laser oscillation with stable resonance.

(Control of Parallel Plate)

The laser apparatus can be configured to control the parallel plate to move for each pulse so that it is capable of producing pulses of two alternating wavelengths. FIG. 2 shows an example of switching the optical paths by controlling the parallel plate to rotate. The optical axis 205, parallel plate 206, first optical path 209, and branch path 207 each correspond to those shown in FIG. 1. Other elements are configured the same as those in FIG. 1. The parallel plate 206 used here is, preferably, circular, with a sector thereof around the rotation axis being chipped.

Figure 2A:
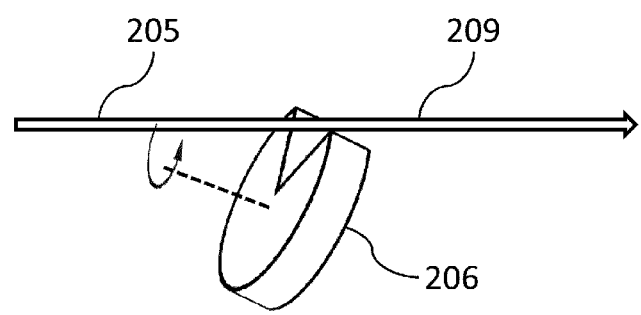
FIG. 2A and FIG. 2B are configuration diagrams illustrating rotation control of a branching optical element.
Figure 2B:
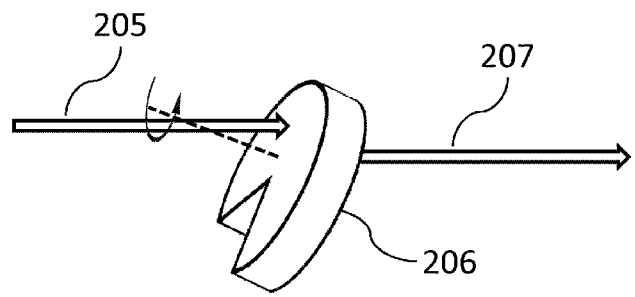

FIG. 2A shows a state where the optical axis 205 does not extend through the parallel plate 206. The optical path in this state is the first optical path 209. FIG. 2B shows a state where the optical axis 205 extends through the parallel plate 206. The optical path in this state is the branch path 207. The branching optical element in these drawings is the partly chipped parallel plate 206, which rotates in its plane around a rotation axis offset from the optical axis 205. When the parallel plate 206 retracts from the optical axis 205, the beam oscillates along the first optical path 209 (coaxial with the optical axis 205) as shown in FIG. 2A, while, when the parallel plate 206 is inserted onto the optical axis 205, the beam oscillates along the branch path 207 as shown in FIG. 2B.

(Control Method of this Embodiment)

The control method of this embodiment will be described with reference to FIG. 1, with an example of a pulsed laser operated at a repeat rate of 10 Hz.

First, the parallel plate is retracted to position 106b so that a beam of a first wavelength oscillates. The laser medium 102 is excited by the light from the pumping light source 101, whereupon a light beam traveling along the first optical path 109 resonates between the output mirror 103 and the reflective mirror 104, and a laser beam of a first wavelength is emitted.

After the emission of the laser beam, when the parallel plate is moved to position 106a, a beam of a second wavelength oscillates. The parallel plate 106 has to be moved after the oscillation of the beam of the first wavelength and before the oscillation of the beam of the second wavelength. For this purpose, the pumping light should preferably be used as a trigger for the position control of the parallel plate. While the wavelength is changed for each pulse in this embodiment, a given wavelength may be oscillated continuously. Namely, with a proper program for controlling the timing of changing the position of the parallel plate 106 as the branching optical element, the wavelengths can be switched per a desired number of pulses.

Embodiment 2

Figure 3A:
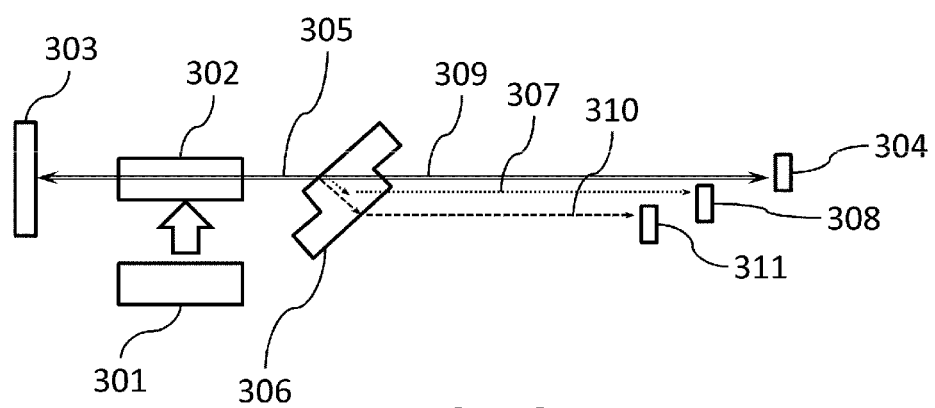
FIG. 3A is a configuration diagram illustrating one embodiment of a laser apparatus of the present invention.

Configuration for Oscillating Beams of Three or More Wavelengths Using a Parallel Plate FIG. 3A is a configuration diagram of a laser resonator in this embodiment.

In this embodiment, a desired one of three wavelengths can be selected with the use of a parallel plate 306. The pumping light source 301 for exciting a laser medium, the laser medium 302, and the output mirror 303 are configured similarly to those of FIG. 1.

Figure 3B:
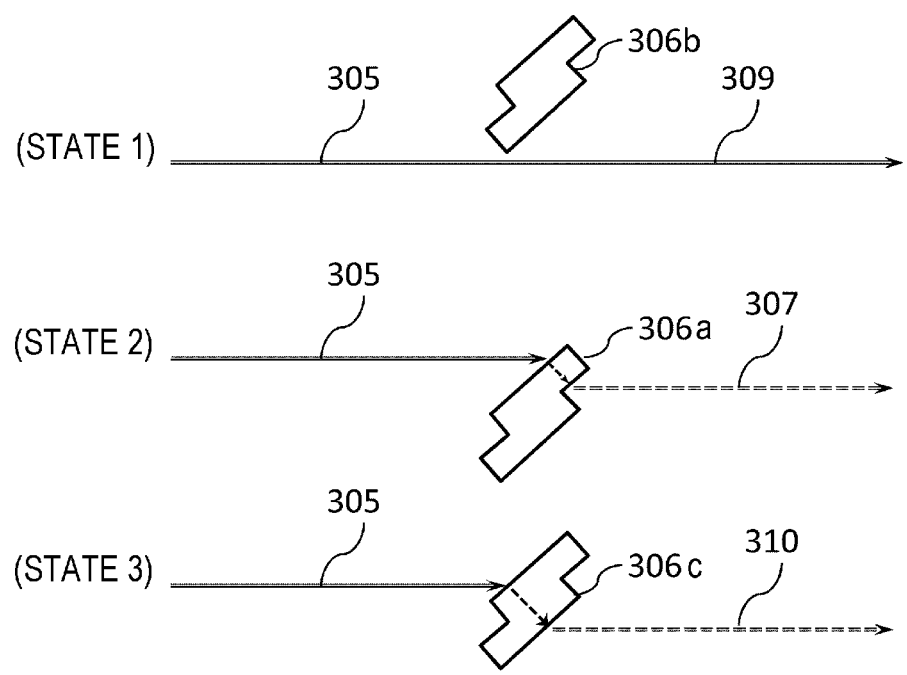
FIG. 3B is a configuration diagram illustrating movement control of a branching optical element.

The parallel plate 306 of this embodiment has portions with different distances between parallel flat surfaces through which the light beam transmits. Such a configuration can be achieved by bonding together two parallel plates offset from each other with an optical contact. The parallel plate 306 can assume three states (positions) shown in FIG. 3B relative to the optical axis 305.

In State 1 (position 306b), the parallel plate 306 is retracted from the optical axis 305. The resonator in this state includes the first optical path 309 through which the light beam of a first wavelength transmits and oscillates, and the reflective mirror 304.

In State 2 (position 306a), the light beam passes through a thin portion of the parallel plate 306. The resonator in this state includes a first branch path 307 through which the light beam of a second wavelength transmits and oscillates, and the reflective mirror 308.

In State 3 (position 306c), the light beam passes through a thick portion of the parallel plate 306. The resonator in this state includes a second branch path 310 through which the light beam of a third wavelength transmits and oscillates, and the reflective mirror 311.

Thus one of the wavelengths can be selected, with reflective mirrors for reflecting light of different wavelengths being provided in respective optical paths.

While one example is shown in this embodiment in which there are three wavelength options, there may be four or more wavelength options by increasing the number of thick portions of the parallel plate.

Embodiment 3

Figure 4:
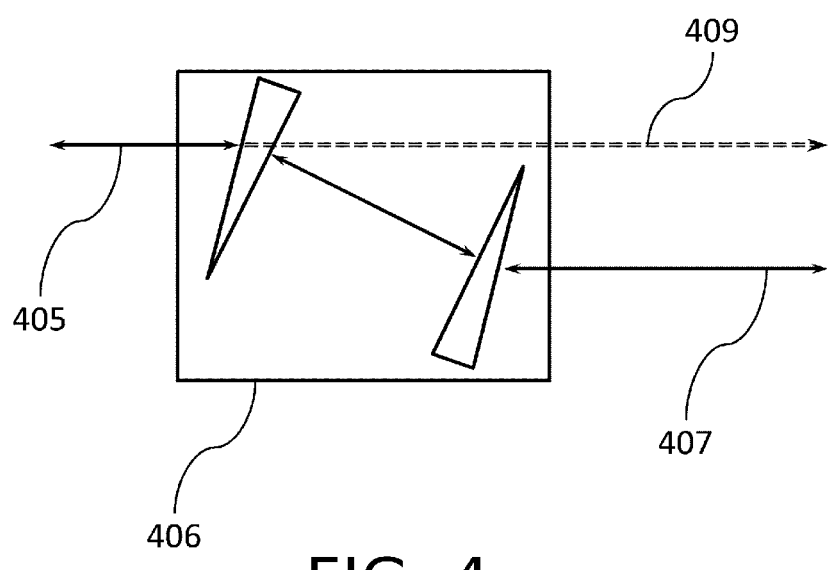
FIG. 4 is a configuration diagram illustrating one embodiment of a branching optical element.

Method of Increasing a Parallel Displacement by Using a Pair of Wedge-Shaped Members In this embodiment, one method of increasing a parallel displacement of the branch path by using a pair of wedge-shaped members as a branching optical element will be described. In FIG. 4, the optical axis 405, branch path 407, and first optical path 409 each correspond to those of FIG. 1.

To increase the parallel displacement only with a parallel plate as in the configurations of Embodiments 1 and 2, the plate thickness must be increased in order to increase the refractive index of the light beam. Instead, in this embodiment, as shown in FIG. 4, a pair of wedge-shaped members 406 are used, which are two identical wedge-shaped members arranged inversely. With this pair of wedge-shaped members 406, when they are retracted from the optical axis 405, the branch path 407 can be displaced from the first optical path 409 largely, while being kept parallel thereto.

With a branching optical element consisting of inversely arranged identical wedge-shaped members, the parallel displacement of the branch path relative to the optical axis can be increased, so that other optical elements can be readily disposed on the optical path. Other optical elements include, for example, an etalon plate added to reduce the line width, or a telescope provided to reduce the thermal lens effect.

Embodiment 4

Method of Increasing a Parallel Displacement by Using Two Parallel Plates

Figure 5:
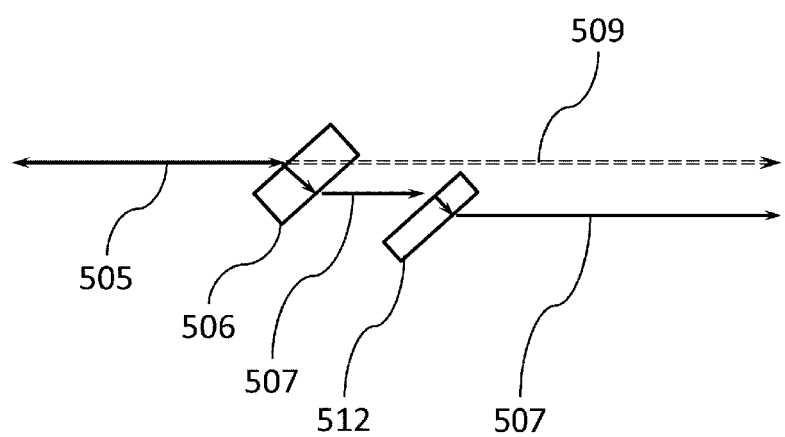
FIG. 5 is a configuration diagram illustrating one embodiment of a branching optical element.

In this embodiment, another method of increasing a parallel displacement will be described with reference to FIG. 5. In the drawing, the optical axis 505, first optical path 509, and branch path 507 are configured the same as those of FIG. 1 and others.

The branching optical element in this embodiment is made up from a movable parallel plate 506 and a second parallel plate 512. The second parallel plate 512 is fixed at a position on the light beam of the branch path 507, and offset from the light beam of the first optical path 509 that is formed when the parallel plate 506 is retracted from the optical axis 505.

With such a configuration, the branch path 507 can be displaced parallel even more, so that the branch path 511 can be formed with an even larger parallel displacement.

Embodiment 5

One Method of Selecting a Wavelength

While variations of branching optical elements for displacing the optical path parallel have been described in the embodiments above, the configurations for selecting a wavelength will be described next.

Figure 6:
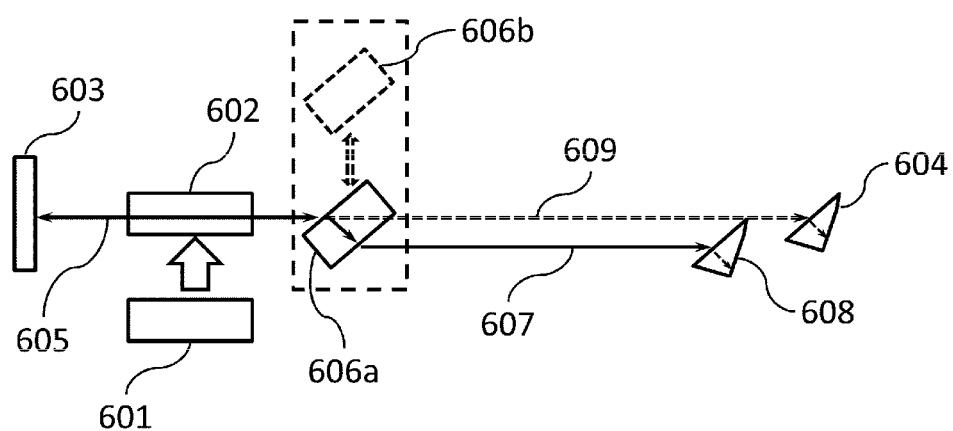
FIG. 6 is a configuration diagram illustrating one embodiment of a laser apparatus of the present invention.

FIG. 6 is a configuration diagram of a laser resonator in this embodiment.

The pumping light source 601, laser medium 602, output mirror 603, optical axis 605, parallel plate 606, and a first optical path 609 and a branch path 607 formed by moving the parallel plate 606 are the same as those of the previously described embodiments.

In this embodiment, prisms 604 and 608 are provided instead of reflective mirrors. The prism 604 forms a resonator between itself and the output mirror 603 when the first optical path 609 is selected. The prism 608 corresponds to the branch path 607. Both prisms therefore have a reflective surface.

In Embodiment 1, a reflective film of dielectric material that reflects light of a desired wavelength is deposited on a reflective mirror so as to produce light of a desired wavelength from a laser medium having a broad gain bandwidth. In this embodiment, instead of the reflective mirrors, prisms having predetermined angles such as to reflect light of a desired wavelength are arranged. The incident surfaces of the prisms are arranged at a pseudo-Brewster angle relative to the light beam.

Each prism is disposed such that, of the light beam that has entered and dispersed in the prism, a beam of a desired wavelength will be incident perpendicularly to the reflective surface of the prism. With the use of a Littrow prism, for example, which has one right triangle surface, precise incidence of light at the Brewster angle is made possible within its machining precision range, by adjusting the angles other than 90° in accordance with the target wavelengths. The prism provides the effect of reducing losses due to the low reflectance even though the light is incident not precisely at the Brewster angle but around the Brewster angle. A reflective film of dielectric material with high reflectance of a target wavelength is formed on the reflective surface of the prism.

With a prism used as the reflection means, as compared to a reflective mirror having a reflective film of dielectric member, the spectral line width of the generated beam can be made narrower.

Variation Example

Figure 7:
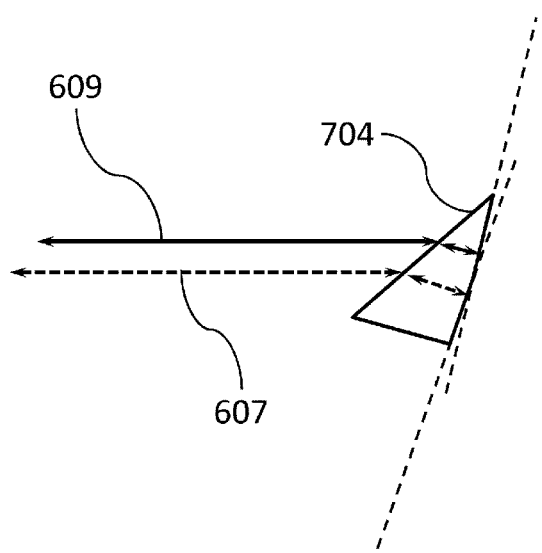
FIG. 7 is a configuration diagram illustrating one embodiment of reflection means.

If the parallel displacement between the first optical path 609 and the branch path 607 is small, a reflective prism 704 having two reflective surfaces of different angles may be used in the reflection unit as shown in FIG. 7 instead of arranging different prisms at the respective optical path ends. The prism 704 shown in FIG. 7 need to be able to make the beams of respective wavelengths reflect and resonate correspondingly to the angular deviation of optical paths that is determined by the refractive index of the prism 704.

Embodiment 6

One Method of Selecting a Wavelength

Figure 8:
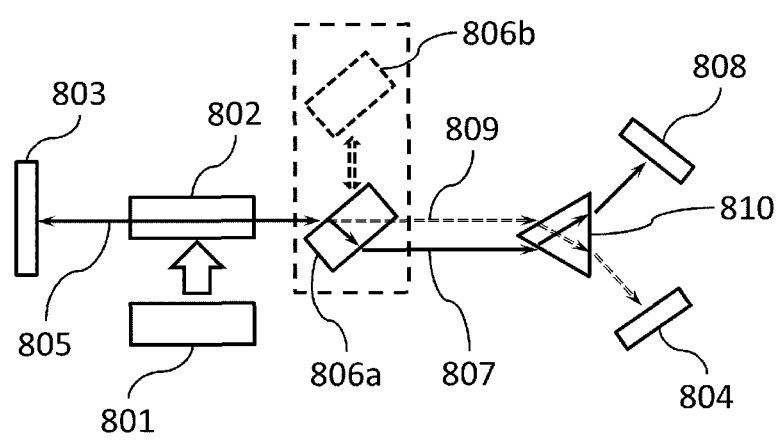
FIG. 8 is a configuration diagram illustrating one embodiment of a laser apparatus of the present invention.

FIG. 8 is a configuration diagram of a laser resonator in this embodiment.

The pumping light source 801, laser medium 802, output mirror 803, optical axis 805, and parallel plate 806 as a branching optical element, are the same as those of the previously described embodiments.

In this embodiment, when the parallel plate 806 is inserted onto the optical axis 805 (position 806a), the light beam passes along the branch path 807, so that a resonator is formed by the output mirror 803 and the reflective mirror 808. When the parallel plate 806 is retracted from the optical axis 805 (position 806b), the optical path coincides with the optical axis 805, so that the light beam passes along the first optical path 809 and a resonator is formed by the output mirror 803 and the reflective mirror 804.

In this embodiment, in particular, a prism 810 for changing the optical path is disposed between the parallel plate 806 and the reflective mirrors 804 and 808. The first optical path 809 and the branch path 807 both enter a first surface and a second surface, which are different surfaces of the prism 810, and emerge from the same third surface.

The prism 810 is arranged at a pseudo-Brewster angle relative to the light beams of the first optical path 809 and the branch path 807. Since reflection losses can be reduced by the pseudo-Brewster angle, the prism 810 need not be coated with a dielectric film on its incident and exit surfaces. With a component that needs to be coated with a dielectric film, the properties of the dielectric film at the ends of the component need to be taken into consideration. Since the prism 810 does not need a dielectric film in this embodiment, it offers the advantage that portions near its ridges can be used. This embodiment is therefore suited to an application where the parallel displacement between the optical paths by the movement of the parallel plate 806 is small.

Of the wavelengths dispersed by the prism 810, only the light of a desired wavelength can be reflected by adjusting the setting positions of the reflective mirrors 804 and 808. Therefore, if the reflective mirrors are to be coated with a reflective film of dielectric material, it should preferably have a high reflectance of a wavelength to be selected.

Embodiment 7

One Embodiment Involving Wavelength Detection

In the embodiments described above, the position of the branching optical element is controlled to select a wavelength to produce light of a predetermined wavelength. Namely, the branching optical element configures a wavelength conversion mechanism. This wavelength conversion mechanism can adopt the following configuration, which makes easy the detection of at what wavelength oscillation is taking place.

Figure 9:
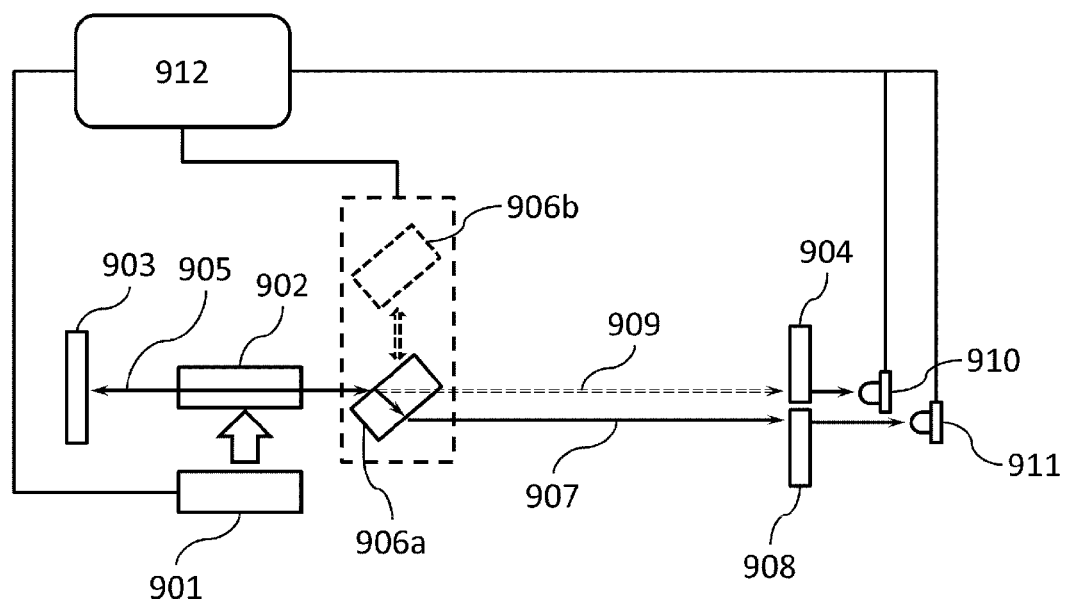
FIG. 9 is a configuration diagram illustrating one embodiment of a wavelength detector.

FIG. 9 shows one embodiment of a method of detecting an oscillating wavelength. The resonator is configured the same as that of FIG. 1. That is, the resonator includes a pumping light source 901, laser medium 902, output mirror 903, reflective mirror 904 or 908, and optical axis 905, and allows selection of one of the branch path 907 and the first optical path 909, with a parallel plate 906 being moved between position 906a and position 906b.

In this embodiment, optical sensors 910 and 911 are disposed at the back (offset from the optical paths) of the reflective mirrors 904 and 908, respectively. The optical sensors detect light leaking form the resonators, to allow determination of in which of the resonators having the first optical path 909 and the branch path 907 oscillation is taking place. A laser controller 912 is a processing device that can control the position of the parallel plate 906 and light emission by the pumping light source 901.

The oscillating wavelength is known by determining the resonator through which the generated light beam is passing, so that wavelength detection is possible with the use of an inexpensive small optical sensor instead of an expensive, large volume apparatus such as a spectrometer. The laser controller 912 can thus perform wavelength conversion appropriately by controlling the position of the parallel plate 906 and light emission by the pumping light source 901 based on the light detection signal inputs.

Embodiment 8

One Embodiment Involving Wavelength Detection

Figure 10:
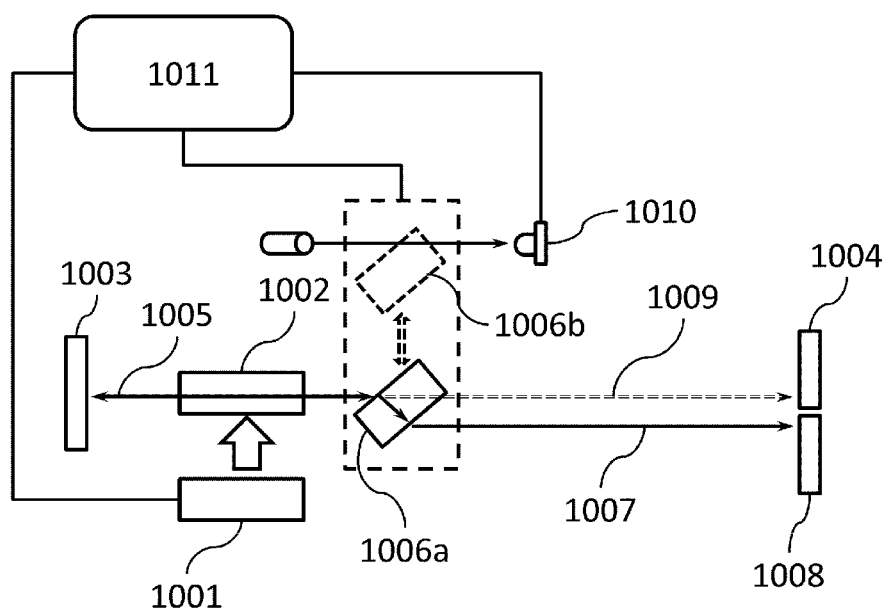
FIG. 10 is a configuration diagram illustrating one embodiment of a wavelength detector.

FIG. 10 shows a method of detecting an oscillating wavelength that is different from Embodiment 7. The difference from Embodiment 7 is that this method uses a photocoupler 1010 instead of the optical sensors 910 and 911 in FIG. 9.

The photocoupler 1010 can detect whether or not the parallel plate 1006 is located at position 1006b out of the optical axis 1005. Since the position of the parallel plate determines the optical path of the laser light, which in turn determines the oscillating wavelength, the oscillating wavelength can be detected as a result of detecting the position of the parallel plate with the photocoupler 1010. This configuration enables detection of an oscillating wavelength with the use of an inexpensive and small photocoupler instead of a spectrometer or the like.

The photocoupler may be arranged such as to detect the position of the parallel plate 1006 inserted onto the optical axis 1005. While FIG. 10 shows a parallel plate controlled to move parallel, a fan-shaped parallel plate such as the one shown in FIG. 2 may also be used, in which case the photocoupler may detect the position of the fan-shaped parallel plate inserted onto the optical axis 1005. The laser controller 1011 can thus perform wavelength conversion appropriately by controlling the position of the parallel plate 1006 and light emission by the pumping light source 1001 based on the detection signal inputs from the photocoupler.

Embodiment 9

One Embodiment Involving Thermal Lens Correction

If the laser apparatus uses alexandrite, the medium should preferably be pumped by a flash lamp, in consideration of the long upper-level life time. Flash lamps are relatively inexpensive excitation means and can favorably be used for applications where high output energy is required. On the other hand, the light use and conversion efficiency in pumping is low due to the broad width of emission spectrum, because of which there is the problem of unnecessary heat generated during the laser oscillation. The heat absorbed in the laser medium changes the refractive index inside the laser medium, causing the thermal lens effect. If the laser medium is alexandrite, it is essential to minimize degradation of the radiation quality caused by the thermal lens effect.

One commonly known simple method for reducing the thermal lens effect is to give a curvature to the reflective surface of a reflective mirror. However, since a thermal lens is created by the pumping energy from the flash lamp, the curvature has to be changed to provide a lens power in accordance with the level of pumping energy. If the lamp energy is changed for each wavelength, this problem cannot be dealt with by a single reflective mirror.

Figure 11:
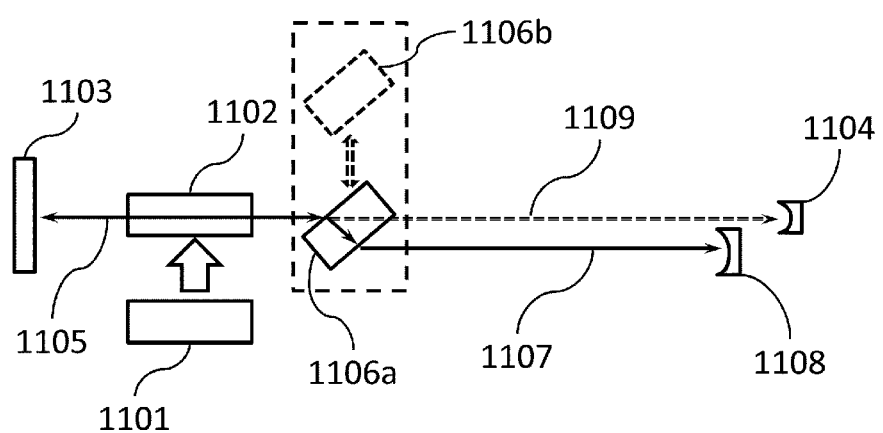
FIG. 11 is a configuration diagram illustrating one embodiment of a thermal lens compensation method.

FIG. 11 shows one embodiment for reducing the thermal lens effect. The resonator is configured substantially the same as that of FIG. 1. That is, the resonator includes a pumping light source 1101, laser medium 1102, output mirror 1103, and reflective mirror 1104. The resonator has the optical axis 1105 between the output mirror 1103 and the reflective mirror 1104. Light is directed through the branch path 1107 to the reflective mirror 1108 when the parallel plate 1106 is inserted onto the optical axis 1105. Light is directed through the first optical path 1109 to the reflective mirror 1104 when the parallel plate 1106 is retracted from the optical axis. The difference from the configuration of FIG. 1 is the shapes and functions of the reflective mirrors 1104 and 1108.

The pumping power of the flash lamp is predetermined for each wavelength. The reflective mirrors 1104 and 1108 have different curvatures that each cancel the effect of thermal lenses formed by respective levels of pumping power. With this embodiment, the thermal lens effect can readily be canceled in a configuration that uses a reflective mirror to select a wavelength.

Embodiment 10

Photoacoustic Apparatus that Uses the Laser Apparatus

In the embodiments described above, various configurations of tunable laser apparatuses that allow stable selection of a wavelength and can be used for a long time without the worries of wavelength shift or optical path angular deviation have been shown.

In this embodiment, one example will be described in which this laser apparatus is applied to a PAT apparatus. Precise measurement is thereby made possible with the use of two or more wavelengths. By determining oxygen saturation of hemoglobin in blood, in particular, functional information of a living body can be extracted. Since the absorption coefficients of oxyhemoglobin and deoxyhemoglobin cross around a wavelength of 800 nm, it is preferable to use a laser apparatus that can emit light of a wavelength band around 800 nm. With the laser apparatus of the present invention that is capable of emitting light of a desired wavelength for each pulse, it is possible to obtain an accurate oxygen saturation distribution with less influence of body movement or the like.

Specific examples of PAT apparatus in this embodiment include the following.

First example is a stationary PAT apparatus having a probe with an ultrasonic element and a laser emission unit incorporated therein for scanning an object fixed in position. Since the laser apparatus of the present invention allows switching of wavelength for each pulse, it is possible to obtain photoacoustic waves generated by light of different wavelengths emitted from substantially the same position even though the moving speed of the probe is increased, whereby a speedy diagnosis is made possible. As photoacoustic waves generated by light of different wavelengths can be obtained substantially at the same time and from the same position, the influence of displacement of measurement position caused by, for example, respiration can be reduced. That is, a comparison between the signals representative of the light of two wavelengths can be made more precise.

A handheld PAT apparatus has also been devised, which has a photoacoustic wave obtaining function added to a conventional ultrasonic diagnosis apparatus. A handheld apparatus has a PAT probe, which is moved by medical personnel in a given area at a given timing. Similarly to the stationary PAT apparatus, the measurement is speeded up and measurement accuracy is enhanced in the handheld PAT apparatus, too, as the wavelength is tunable per pulse.

In the PAT apparatus equipped with the laser apparatus of the present invention capable of wavelength selection with high oscillation stability, stable pulsed oscillation is possible and the repeat rate can be increased without consideration of instability. The apparatus allows versatile use due to its reliable oscillation stability even in applications where the wavelength is switched per several or several tens pulses.

Example

An example will be shown below, where the laser apparatus of the present invention is applied to a medical PAT apparatus.

Figure 12:
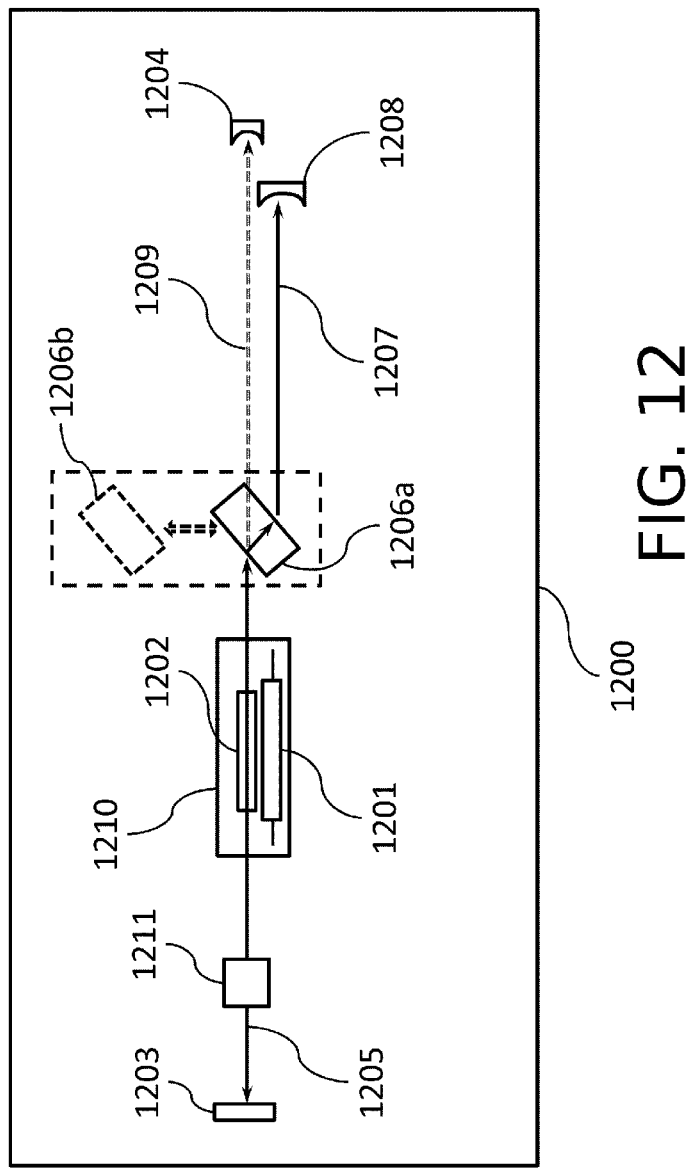
FIG. 12 is a configuration diagram illustrating one embodiment of a photoacoustic apparatus of the present invention.

FIG. 12 is a schematic diagram of a laser apparatus incorporated in a medical PAT apparatus 1200. This laser apparatus has an alexandrite crystal as the laser medium and is capable of lasing at wavelengths of 800 nm and 755 nm. The medium is excited by pumping light repeatedly at a frequency of 10 Hz.

The laser apparatus is configured as follows. Inside a pumping chamber 1210 are arranged a flash lamp 1201 that excites alexandrite and an alexandrite crystal 1202. The parallel plate 1206 is made of synthetic quartz having a thickness of 30 mm, with both surfaces optically polished to have a flatness of λ/20 and parallelism of 1 arc second or less. The parallel plate 1206 is arranged at a Brewster angle relative to the optical path of a generated laser beam. The output mirror 1203 is coated with a dielectric film having a transmissivity of 40% to light of wavelengths of 800 nm and 755 nm. The reflective mirror 1204 is coated with a reflective film of dielectric material having high reflectance to light of a center wavelength of 800 nm, and the reflective mirror 1208 is coated with a reflective film of dielectric material having high reflectance to light of a center wavelength of 755 nm. A Q-switch 1211 consisting of a Pockels cell is disposed on the optical axis 1205 between the output mirror 1203 and the pumping chamber 1210.

When the parallel plate 1206 is retracted from the optical axis 1205 (position 1206b), the light beam travels along the first optical path 1209 that coincides with the optical axis 1205. Light produced at this time has a wavelength of 800 nm. When the parallel plate 1206 is inserted onto the optical axis 1205 (position 1206a), the light beam travels along the branch path 1207. Light produced at this time has a wavelength of 755 nm. The branch path 1207 formed when the parallel plate 1206 is inserted is parallel to the first optical path 1209, and the reflective surfaces of the reflective mirrors 1204 and 1208 are perpendicular to the optical axis 1205.

(Step 1: Oscillation at 800 nm Wavelength for First Pulse)

The flash lamp is turned on when the parallel plate is at position 1206b. The Q-switch 1211 initiates lasing after 150 µs, when the energy output triggered by the lamp reaches the peak. The light beam resonating between the output mirror 1203 and the reflective mirror 1204 is then radiated, with a wavelength of 800 nm, pulse width of 50 ns, energy of 150 mJ/pulse, and spectral line width of 8 nm (full width at half maximum).

(Step 2: Oscillation at 755 nm Wavelength for Second Pulse)

The parallel plate is then moved parallel to position 1206a. The flash lamp is turned on. The lamp is turned on at a repeat rate of 10 Hz. The Q-switch initiates lasing after 150 µs after the light emission. The light beam resonates in the resonator consisting of the output mirror 1203 and the reflective mirror 1208, passing along the branch path 1207. The light beam has a wavelength of 755 nm, pulse width of 50 ns, energy of 200 mJ/pulse, and spectral line width of 8 nm (full width at half maximum).

The process returns to Step 1, to produce a pulse of 800 nm wavelength again. Light pulses were produced alternately at two different wavelengths by this sequence, with the stable oscillation characteristics mentioned above at each wavelength.

A measurement of the energy spread showed that the output energy stability (RMS) was 1% at each wavelength, which was the same as at each wavelength measured without moving the parallel plate. The wavelength stability was such that no fluctuations were detected in both wavelengths in a measurement with a spectrometer having a resolution of 1 nm. This laser uses a parallel plate that hardly affects the lasing properties for the wavelength conversion mechanism, so that it has excellent long term stability, and it is very unlikely that a misalignment or the like occurs in the resonator. As the laser is formed by optical elements having a high energy damage threshold, the optical elements inside the resonator cause less optical energy loss. Highly efficient high energy emission is thus made possible.

The laser apparatus in this example is configured by encasing the resonator described above in a housing with an anti-vibration mechanism and caster wheels. A stationary PAT apparatus was set up, with this laser apparatus combined with a mechanism for retaining an object such as a living body in position, and a probe or the like movable on the stationary object for scanning. The PAT apparatus also includes an information processing device that generates property information of the inside of the object based on the photoacoustic waves obtained by the probe.

A relatively wide measurement area of a pseudo living body sample having blood vessels with pseudo oxyhemoglobin and deoxyhemoglobin was scanned by the stationary PAT apparatus. Light pulses were produced alternately at 800 nm and 755 nm in the measurement to obtain wavelength-specific functional information. As a result, highly accurate functional information was obtained, with little influence on the obtained signals of positional displacement or incorrect timing of measurement. Namely, it was shown that the laser apparatus of the present invention could be used to configure a PAT apparatus that can operate stably in a hospital.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-220134, filed on Oct. 2, 2012, which is hereby incorporated by reference herein in its entirety.

What is claimed is:

1. A laser apparatus that allows selection of a wavelength of output light from a plurality of options, comprising:
   a resonator made up from an output mirror and a reflection means having a plurality of reflective surfaces fixed in position;
   a laser medium disposed on an optical axis inside the resonator;
   a branch means branching an optical path of a light beam formed on the optical axis when light oscillates from the laser medium into a plurality of optical paths having an end at one reflective surface of the reflection means, the branch means forming a first optical path coinciding with the optical axis when located out of the optical axis, and forming a branch path by moving the light of the optical axis parallel when located on the optical axis; and
   a moving means moving the branch means between a position on the optical axis and a position out of the optical axis,
   wherein the reflective surface determining a wavelength of output light.

2. The laser apparatus according to claim 1, wherein the branch means is a parallel plate that moves the optical path on the optical axis parallel by refraction.

3. The laser apparatus according to claim 2, wherein the moving means controls the parallel plate to move parallel.

4. The laser apparatus according to claim 2, wherein the moving means controls the parallel plate to rotate.

5. The laser apparatus according to claim 1, wherein
   the branch means is a component that has a plurality of flat plates with different thicknesses, and forms a plurality of branch paths with different parallel displacements of the light in accordance with the thicknesses, and
   the reflection means has reflective surfaces corresponding to respective branch paths.

6. The laser apparatus according to claim 1, wherein the branch means is a pair of identical wedge-shaped members that are arranged inversely.

7. The laser apparatus according to claim 1, wherein the branch means further includes a parallel plate fixedly arranged on an optical path that is formed when the branch means is located at the position on the optical axis.

8. The laser apparatus according to claim 1, wherein the plurality of reflective surfaces of the reflection means include a reflective film of dielectric material that reflects light of a wavelength corresponding to each of the reflective surfaces.

9. The laser apparatus according to claim 8, wherein the reflective surfaces of the reflection means each have a curvature that is set to reduce thermal lens effects for corresponding wavelengths.

10. The laser apparatus according to claim 1, wherein the reflection means is a prism arranged for each of the plurality of optical paths for reflecting light of a wavelength corresponding to the branch path.

11. The laser apparatus according to claim 1, wherein the reflection means is a prism having reflective surfaces of different angles corresponding to each of the plurality of optical paths.

12. The laser apparatus according to claim 1, further comprising:
   a prism for changing the optical path that is arranged between the branch means and the reflection means and that includes a first surface for a light beam from the first optical path to enter, a second surface for a light beam from the branch path to enter, and a third surface for light beams that have entered the first surface and the second surface to exit,
   wherein the light beams exiting from the third surface each entering a different reflective surface of the reflection means.

13. The laser apparatus according to claim 1, further comprising:
   an optical sensor that detects light leaking from respective reflective surfaces of the reflection means to allow control of light emission based on a wavelength corresponding to the reflective surface from which the light is detected.

14. The laser apparatus according to claim 1, further comprising:
   a photocoupler that detects whether or not the branch means is located out of the optical axis to allow control of light emission based on a wavelength determined by where the branch means is located.

15. A photoacoustic apparatus comprising
the laser apparatus according to claim 1, and
an information processing device generating property information of inside of an object based on a photoacoustic wave generated when the object is irradiated with light from the laser apparatus.

16. A laser apparatus that allows selection of a wavelength of output light from a plurality of options, comprising:
a resonator comprising an output minor and a reflection means having a plurality of reflective surfaces fixed in position;
a laser medium disposed on an optical axis inside the resonator;
a branch means branching an optical path of a light beam formed on the optical axis when light oscillates from the laser medium into a plurality of optical paths having an end at one reflective surface of the reflection means, the branch means forming a first optical path when located out of the optical axis, and forming a second optical path when located on the optical axis, a reflective surface in the first optical path being different from a reflective surface in the second optical path; and
a moving means moving the branch means between a position on the optical axis and a position out of the optical axis,
wherein the reflective surface determining a wavelength of output light.

17. A laser apparatus that allows selection of a wavelength of output light from a plurality of options, comprising:
a resonator comprising an output minor and a reflection means having a plurality of reflective surfaces fixed in position;
a laser medium disposed on an optical axis inside the resonator;
a branch means branching an optical path of a light beam formed on the optical axis when light oscillates from the laser medium into a plurality of optical paths having an end at one reflective surface of the reflection means, the branch means forming a first optical path when located at a first position, and forming a second optical path when located at a second position other than the first position; and
a moving means moving the branch means between a first position and a second position.

18. A laser apparatus comprising:
an mirror;
a reflection means having a plurality of reflective surfaces fixed in position, the plurality of reflective surfaces having different reflective characteristics;
a laser medium arranged between the mirror and the reflection means with respect to an optical path of a light from the laser medium;
a switch means switching a plurality of optical paths having an end at one reflective surface of the reflection means, each of the optical paths corresponding to one of the of reflective surfaces; and
a moving means moving the switch means so that the switch means switches a plurality of optical paths.

19. The laser apparatus according to claim 18, wherein the moving means controls the switch means to move parallel.

20. The laser apparatus according to claim 19, wherein the moving means controls the switch means to move parallel to a vertical component to at least one optical path from among the plurality of optical paths.

21. The laser apparatus according to claim 19, wherein the moving means controls the switch means to move parallel between a position to which a light from the laser medium enters and a position to which a light from the laser medium does not enter.

22. The laser apparatus according to claim 19, wherein the switch means comprises a parallel plate.

23. The laser apparatus according to claim 19, wherein the switch means comprises a pair of identical wedge-shaped members that are arranged inversely.

24. The laser apparatus according to claim 18, wherein the moving means rotates the switch means.

25. The laser apparatus according to claim 24, wherein the moving means rotates the switch means, and
an axis of rotation is a direction not vertical to at least one optical path from among the plurality of optical paths.

26. The laser apparatus according to claim 25, wherein the moving means rotates the switch means so that the switch means switches the light from the laser medium between a status in which the light enters to the switch means and a status in which the light does not enter to the switch means.

27. The laser apparatus according to claim 24, wherein the switch means has a parallel plate which has an opening therein.

28. The laser apparatus according to claim 18, wherein each of the reflective surfaces of the reflection means has different curvature.

29. The laser apparatus according to claim 18, further comprising:
an optical sensor detecting light leaking from respective reflective surfaces of the reflection means; and
a laser controller controlling at least one of a position of the switch means and a pumping light source, based on the light detected by the optical sensor.

30. The laser apparatus according to claim 18, further comprising:
a detecting device detecting a position of the switch means; and
a laser controller controlling at least one of the position of the switch means and a pumping light source, based on the position detected by the detecting device.

31. A photoacoustic apparatus comprising:
the laser apparatus according to claim 18; and
an information processing device generating property information of inside of an object based on a photoacoustic wave generated when the object is irradiated with light from the laser apparatus.

* * * * *